United States Patent
Takahashi et al.

(10) Patent No.: US 9,804,053 B2
(45) Date of Patent: Oct. 31, 2017

(54) DEFECT ANALYSIS DEVICE, DEFECT ANALYSIS METHOD, AND PROGRAM

(71) Applicant: NEC Corporation, Tokyo (JP)

(72) Inventors: Masatake Takahashi, Tokyo (JP); Mizuho Tomiyama, Tokyo (JP); Yasuhiro Sasaki, Tokyo (JP)

(73) Assignee: NEC Corporation, Tokyo (JP)

( * ) Notice: Subject to any disclaimer, the term of this patent is extended or adjusted under 35 U.S.C. 154(b) by 288 days.

(21) Appl. No.: 14/431,809

(22) PCT Filed: Sep. 13, 2013

(86) PCT No.: PCT/JP2013/074927
§ 371 (c)(1),
(2) Date: Mar. 27, 2015

(87) PCT Pub. No.: WO2014/050619
PCT Pub. Date: Apr. 3, 2014

(65) Prior Publication Data
US 2015/0276545 A1  Oct. 1, 2015

(30) Foreign Application Priority Data
Sep. 28, 2012 (JP) .................. 2012-216890

(51) Int. Cl.
*G01N 29/04* (2006.01)
*G01N 29/28* (2006.01)
(Continued)

(52) U.S. Cl.
CPC ............ *G01M 5/0025* (2013.01); *F17D 5/06* (2013.01); *G01M 3/00* (2013.01); *G01M 3/243* (2013.01);
(Continued)

(58) Field of Classification Search
CPC .... G01M 5/0025; G01M 5/0033; G01M 7/02; G01M 3/00; G01N 29/04; G01N 29/341; G01N 29/28
(Continued)

(56) References Cited

U.S. PATENT DOCUMENTS 3,462,240 A   8/1969  Bosselaur et al.
4,172,379 A * 10/1979  Van Tilburg .......... G01M 3/246
                                                    346/33 F
(Continued)

FOREIGN PATENT DOCUMENTS

EP   0 091 087 A1   10/1983
GB   2 406 654 A    4/2005
(Continued)

OTHER PUBLICATIONS

International Search Report and Written Opinion mailed Nov. 26, 2013 in corresponding PCT International Application.
(Continued)

*Primary Examiner* — J M Saint Surin
(74) *Attorney, Agent, or Firm* — Finnegan, Henderson, Farabow, Garrett & Dunner, L.L.P.

(57) ABSTRACT

The present invention provides a defect analysis device including: an excitation unit (107) that imparts vibrations of a plurality of frequencies to a fluid (110) flowing through a pipe (108); a first detector (106) that, when the excitation part (107) is imparting vibrations, detects vibrations emanating from the pipe (108); and a signal processing unit (101) that extracts a feature quantity from a vibration waveform acquired by the first detector (106), and uses the extracted feature quantity to estimate the extent of a defect formed in the pipe (108).

20 Claims, 14 Drawing Sheets

(51) Int. Cl.
    *G01N 29/34* (2006.01)
    *G01M 3/00* (2006.01)
    *G01M 5/00* (2006.01)
    *G01M 7/02* (2006.01)
    *G01M 3/24* (2006.01)
    *F17D 5/06* (2006.01)

(52) U.S. Cl.
    CPC ............ *G01M 5/0033* (2013.01); *G01M 7/02* (2013.01); *G01N 29/04* (2013.01); *G01N 29/28* (2013.01); *G01N 29/341* (2013.01)

(58) Field of Classification Search
    USPC .......................................................... 73/592
    See application file for complete search history.

(56) References Cited

U.S. PATENT DOCUMENTS

| | | | | |
|---|---|---|---|---|
| 4,554,941 A | * | 11/1985 | Coon | F16L 55/24 137/13 |
| 6,186,004 B1 | * | 2/2001 | Kaduchak | G01N 29/036 73/596 |
| 6,415,666 B1 | * | 7/2002 | Donskoy | F41H 11/12 367/87 |
| 7,810,378 B2 | * | 10/2010 | Hunaidi | G01M 3/243 73/40.5 A |
| 2012/0007743 A1 | * | 1/2012 | Solomon | G01M 3/243 340/605 |

FOREIGN PATENT DOCUMENTS

| | | | |
|---|---|---|---|
| GB | 2406654 | * | 4/2005 |
| GB | 2421311 A | * | 6/2006 |
| JP | 60-238734 | | 11/1985 |
| JP | 10-281921 | | 10/1998 |
| JP | 11-142280 | | 5/1999 |
| JP | 02000131292 A | * | 5/2000 |
| JP | 2000-310577 | | 11/2000 |
| JP | 2001-280943 | | 10/2001 |
| JP | 2009-002873 | | 1/2009 |
| JP | 2009002873 | * | 1/2009 |
| JP | 2010-169626 | | 8/2010 |
| JP | 2010256246 | * | 11/2010 |
| KR | 101038005 B1 | * | 6/2011 |

OTHER PUBLICATIONS

Extended European Search Report mailed on Apr. 7, 2016, by the European Patent Office in counterpart European Patent Application No. 13840363.9.

* cited by examiner

Fig. 12

| PIPE WALL THICKNESS (mm) | PEAK FREQUENCY (Hz) | DIAMETER OF HOLE (mm) |
|---|---|---|
| 5 | ○○○~××× | 5 |
| 5 | ×××~△△△ | 4 |
| .... | .... | .... |
| 10 | □□□~●●● | 5 |
| .... | .... | .... |

Fig. 13

| PIPE WALL THICKNESS (mm) | SHARPNESS | DIAMETER OF HOLE (mm) |
|---|---|---|
| 5 | ○○~×× | 5 |
| 5 | ××~△△ | 4 |
| .... | .... | .... |
| 10 | □□~●● | 5 |
| .... | .... | .... |

Fig. 14

| INFORMATION ABOUT PIPE | | | PEAK FREQUENCY (Hz) | PEAK FREQUENCY (mm) |
|---|---|---|---|---|
| MATERIAL | PIPE WALL THICKNESS (mm) | ... | | |
| ○○ | 5 | ... | ○○○~×××<br>○○○~×××  | 5 |
| ○○ | 5 | ... | ×××~△△△ | 4 |
| .... | .... | .... | .... | .... |
| ×× | 10 | ... | □□□~●●● | 5 |
| .... | .... | .... | .... | .... |

DEFECT ANALYSIS DEVICE, DEFECT ANALYSIS METHOD, AND PROGRAM

CROSS-REFERENCE TO RELATED PATENT APPLICATIONS

This application is a National Stage Entry of International Application No. PCT/JP2013/074927, filed Sep. 13, 2013, which claims priority from Japanese Patent Application No. 2012-216890, filed Sep. 28, 2012. The entire contents of the above-referenced applications are expressly incorporated herein by reference.

TECHNICAL FIELD

The present invention relates to a defect analysis device, a defect analysis method, and a program.

BACKGROUND ART

With the progress of IT and network technology supported by digitalization, an amount of information processed by a person and an electronic device and stored is steadily increasing. Correct data on a phenomenon is acquired by a sensor that is an input device, correctly analyzed, assessed, processed, and recognized as useful information by a person. This is positioned as important activities for constructing a secure and safe society to a human society which becomes unconnected to a large amount of information.

In a modern life, facilities such as a water supply and sewerage network, a high-pressure chemical pipeline for gas, petroleum, or the like, a high-speed railway, a long span bridge, a tower building, a large commercial airplane, a car, and the like are created and used as the infrastructure of an affluent society. If these facilities are broken by natural disaster such as an unexpected earthquake or the like or aged deterioration and this results in a major accident, the accident has a lot of influence on the society and an economic loss is large. Deterioration due to corrosion, abrasion, backlash, or the like of a member used for the facility increases with the time. Lastly, malfunction such as breaking or the like occurs. In order to secure the safety and security of the facilities, many efforts are focused on the technical development beyond the academic areas of science, engineering, social science, and the like. A non-destructive testing technology in which a test can be performed at low cost and by a simple operation becomes important to prevent the major accident due to deterioration and breaking of the facilities.

By the way, as a liquid leakage test performed to detect liquid leakage due to deterioration or breaking of a pipe, a check by ear in which a person hears the sound generated by the leakage is usually used.

However, in many cases, the pipe is buried in the ground or installed on a high place of a building. Therefore, it is dangerous to perform the check by ear and requires a lot of labor. For this reason, the check cannot be performed with high accuracy and cannot be sufficiently performed. Further, a degree of proficiency of a checker has an influence on the accuracy of the result. Currently, because the degree of proficiency of the checker is low, it is difficult to prevent a leakage accident.

Further, when water leak is detected, it is required to specify the location of the leakage with a high degree of accuracy to reduce a repair cost. Today, a specialized checker specifies the location by the check by ear.

However, when an external noise such as a traffic noise generated by traffic or the like exists and a frequency component of the sound generated by the water leak is similar to that of the external noise, the check is disturbed by the external noise and it becomes difficult to determine whether the water leak occurs. For this reason, some countermeasures are taken, for example, the check is performed in a midnight time zone in which the external noise hardly occurs. However, the checker is greatly burdened by this.

In order to solve such problem, various leakage check methods using an instrument are proposed.

Patent Literature 1 (PTL1) discloses a leakage detection device composed of a vibration detection device having a pickup including a piezoelectric element, a detection device main body including a voltage amplifier which performs voltage amplification of an output signal and a plurality of kinds of noise elimination means which eliminate noise from the output signal, and a headphone.

Patent Literature 2 (PTL2) discloses a leak amount measuring device including a video observation device which observes a video of a leaking fluid, a sound measuring device which measures sound of the leaking fluid, a feature amount extraction device which extracts a feature amount of the leaking fluid from the outputs of the video observation device and the sound measuring device, and a leak amount retrieval device which calculates a leak amount by retrieving a database related to the leak amount that is created for each of pressure and temperature of the fluid, a phase state, and an area, a shape, or the like of a leak part.

Patent Literature 3 (PTL3) discloses a water leak detection method of which a water pipe and water in this water pipe are excited by a sound wave emitted by a sound wave source installed to a branch pipe laid on the ground that is connected to a water pipe buried in the ground, the sound wave is detected by a sound wave receiver on the surface of the ground, a signal processing of the detection signal of the sound wave is performed in synchronization with an excitation signal of the sound wave source, and water leak is detected based on a phenomenon in which the level of the detection signal changes according to the presence or absence of water leak.

CITATION LIST

Patent Literature

[PTL 1] Japanese Patent Application Laid-Open No. 2009-002873
[PTL 2] Japanese Patent Application Laid-Open No. 2000-310577
[PTL 3] Japanese Patent Application Laid-Open No. Sho 60-238734

SUMMARY OF THE INVENTION

Technical Problem

The inventors of this present application expects that when not only the presence or absence of a defect of a pipe and the location of a defect but also a degree of defect can be specified with a high degree of accuracy, urgency of repair work to repair each defect and the like can be appropriately grasped and whereby, a predetermined countermeasure can be implemented before the major accident occurs and the defect that causes the major accident can be reduced.

The technologies described in Patent Literature 1 (PTL1) and Patent Literature 3 (PTL3) are used for detecting the presence or absence of fluid leak and specifying the location of the defect. Therefore, the degree of defect cannot be specified by using these technologies.

In the technology described in Patent Literature 2 (PTL2), the sound and the video of the leaking fluid are measured and the leak amount is specified by using the feature amount. However, when this technology is used, the accuracy of the measured data of the sound and the like of the leaking fluid is low. Accordingly, the accuracy of the leak amount specified based on the data is also low. For example, when the external noise such as a traffic noise or the like exists and a frequency component of the sound generated by the water leak is similar to that of the external noise, it becomes difficult to determine the leak amount.

An object of the present invention is to provide a technology to specify the degree of defect of the pipe with a high degree of accuracy.

Solution to Problem

By the present invention, a defect analysis device including vibration means which apply vibration with a plurality of frequency components to at least one of fluid flowing in a pipe and the pipe, first detection means which detect the vibration applied by the vibration means, and signal processing means which extract a feature amount from a vibration waveform acquired by the first detection means and estimate a degree of defect formed in the pipe by using the extracted feature amount is provided.

Further, by the present invention, a defect analysis method of which a computer executes a vibration step of applying vibration with a plurality of frequency components to at least one of fluid flowing in a pipe and the pipe, a first detection step of detecting the vibration applied in the vibration step, and a signal processing step of extracting a feature amount from a vibration waveform acquired in the first detection step and estimating a degree of defect formed in the pipe by using the extracted feature amount is provided.

By the present invention, a program which causes a computer to function as vibration means which apply vibration with a plurality of frequency components to at least one of fluid flowing in a pipe and the pipe, first detection means which detect the vibration applied by the vibration means, and signal processing means which extract a feature amount from a vibration waveform acquired by the first detection means and estimate a degree of defect formed in the pipe by using the extracted feature amount is provided.

Advantageous Effects of Invention

By the present invention, a technology to specify the degree of defect in the pipe with a high degree of accuracy can be realized.

BRIEF DESCRIPTION OF DRAWINGS

The above-mentioned object, the other object, features, and advantages of the present invention will be apparent from the following description of the preferred exemplary embodiments and the following accompanying drawings thereof.

FIG. 12 shows an example of reference data of an exemplary embodiment.

FIG. 13 shows an example of reference data of an exemplary embodiment.

FIG. 14 shows an example of reference data of an exemplary embodiment.

DESCRIPTION OF EMBODIMENTS

An exemplary embodiment of the present invention will be described below with reference to a drawing.

Further, a device according to this exemplary embodiment is realized by an arbitrary combination of hardware which mainly includes a CPU in an arbitrary computer, a memory, a program loaded in the memory (including a program stored in the memory in advance before delivery of the device and a program downloaded from a storage medium such as a CD or the like or a server or the like on the Internet), a storage unit such as a hard disk or the like for storing the program, and an interface for network connection and software. It is understood by the person skilled in the art that a method for realizing the device and the device include various modifications.

In a functional block diagram used for explaining the exemplary embodiment, each block is a functional block and it does not represent a hardware unit. It is shown in these figures that each device is realized as one device. However, a method for realizing each device is not limited to this method. Namely, each device may be realized by two or more physically separated devices or two or more logically separated devices.

(First Exemplary Embodiment)

Figure 1:
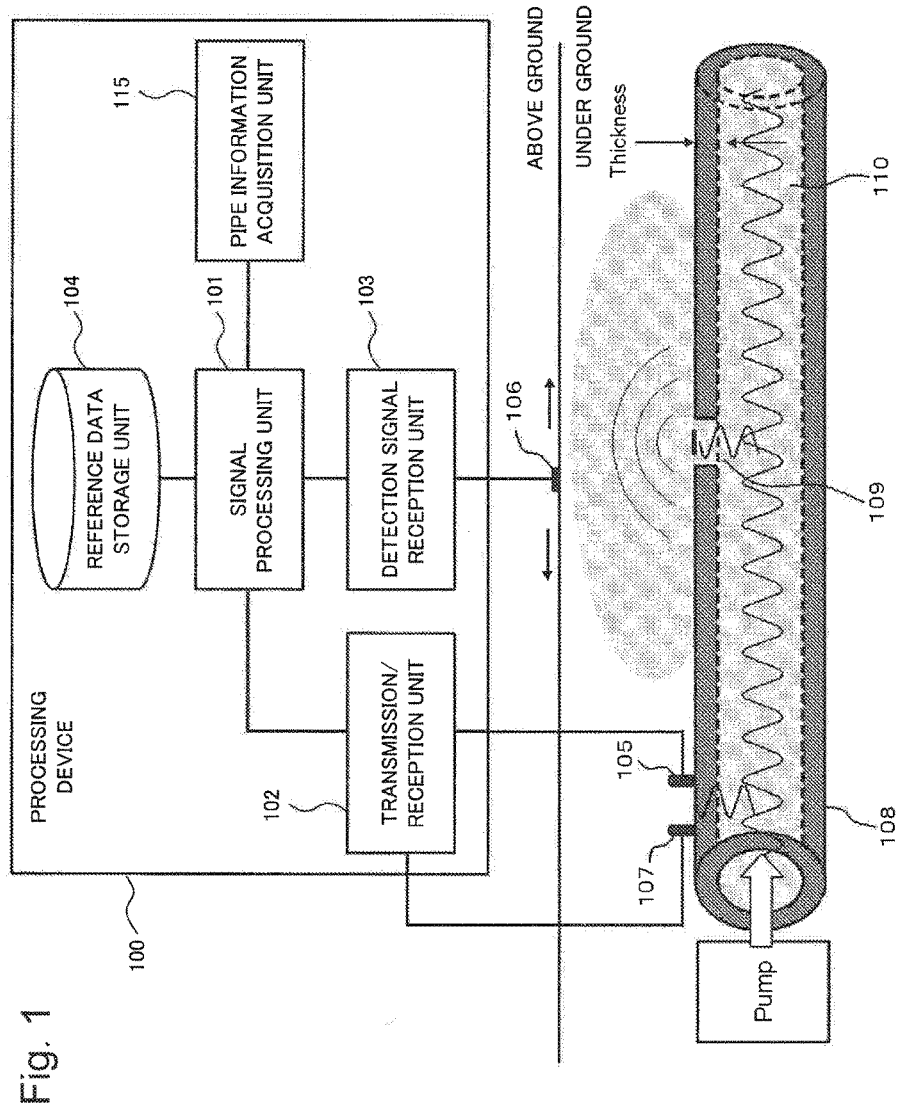
FIG. 1 is an example of a conceptual rendering of a defect analysis device according to an exemplary embodiment.

FIG. 1 shows an example of a conceptual rendering of a defect analysis device according to a first exemplary embodiment.

The defect analysis device includes a vibration unit 107, a first detection unit 106, a second detection unit 105, and a processing device 100. The processing device 100 includes a signal processing unit 101, a transmission/reception unit 102, a detection signal reception unit 103, a reference data storage unit 104, and a pipe information acquisition unit 115. The processing device 100 is connected to the vibration unit 107, the first detection unit 106, and the second detection unit 105 so as to be communicable to each other through a wired or wireless connection and the processing device 100 can transmit/receive predetermined information to/from the vibration unit 107, the first detection unit 106, and the second detection unit 105.

The vibration unit 107 and the second detection unit 105 are installed on an outer surface of a pipe 108 installed in the ground. The vibration unit 107 and the second detection unit 105 may be permanently installed on the outer surface of the pipe 108. The first detection unit 106 is installed on the surface of the ground. An installation location of the processing device 100 is not limited in particular. For example, it is installed on the ground.

Here, a concept of the exemplary embodiment will be described briefly.

As shown in FIG. 1, when the pipe 108 filled with fluid 110 has a defect (such as a hole or the like) through which the fluid leaks, a predetermined amount of fluid 110 is pushed out through the defect (such as the hole or the like) of the pipe 108 according to a pressure applied by a pump which sends the fluid 110 out and the shape, the size, or the like of the defect and whereby, a leak part 109 is generated. In this case, the pressure is applied to the fluid 110 and the pipe 108 by the flow of the fluid 110 and the vibration is excited. The generated vibration propagates along the pipe 108 and the fluid 110 for example, in the horizontal direction of FIG. 1. In this exemplary embodiment, this vibration is detected by the second detection unit 105 and the detection signal is analyzed. Whereby, it is detected that the leak part 109 (defect) is formed in the pipe 108.

Further, the vibration generated when the fluid 110 leaks from the leak part 109 is propagated to the outside of the pipe 108 by the fluid 110 leaking from the leak part 109. In this exemplary embodiment, the vibration with a sufficiently large amplitude is applied to the pipe 108 by the vibration unit 107. The vibration applied to the pipe 108 is also transmitted to the fluid 110 flowing in the pipe 108. The vibration propagates through the pipe 108 and the fluid 110 in the pipe 108. In this exemplary embodiment, the amplitude of the vibration is set so that when the vibration propagates to the outside of the pipe 108 through the leak part 109 and transmits through the ground, the vibration with a sufficiently large amplitude reaches the surface of the ground. In this exemplary embodiment, the vibration which reaches the surface of the ground is detected by the first detection unit 106 and the detection signal is analyzed. Whereby, the location of the leak part 109 (defect) is specified and a degree of defect is estimated.

Each unit will be described in detail below.

The second detection unit 105 detects at least one of the vibration propagating through the pipes 108 and the vibration propagating through the fluid 110 flowing in the pipes 108. More specifically, the second detection unit 105 detects at least one of the vibration propagating through the pipes 108 and the vibration propagating through the fluid 110 flowing in the pipes 108 that are generated when the fluid leaks from the leak part 109 formed in the pipe 108. In a case of an example shown in FIG. 1, the second detection unit 105 is attached on the outer surface of the pipe 108 and detects the vibration propagating through the pipe 108.

As the second detection unit 105, for example, a sensor for measuring vibration of a solid can be used. A piezoelectric acceleration sensor, an electrodynamic acceleration sensor, a capacitance type acceleration sensor, an optical velocity sensor, a dynamic strain sensor, or the like can be used for the sensor for measuring vibration of a solid. For example, in a case in which the fluid 110 is water and the pipe 108 is a steel pipe, the vibration generated when water leaks has a frequency component of several 10 Hz to several kHz. The piezoelectric acceleration sensor is suitable for detection of such vibration. For attaching the second detection unit 105 on the surface of the pipe 108, for example, a magnet, a dedicated jig, or an adhesive material can be used.

For example, the second detection unit 105 is permanently attached on the outer surface of the pipe 108 and measures the vibration propagating through the pipe 108 at all times or intermittently (for example, one time a day, one time an hour, ten times every three minutes, or the like). Data of measured vibration is transmitted to the transmission/reception unit 102 of the processing device 100 described later.

Further, although not shown in FIG. 1, a plurality of second detection units 105 may be installed on the outer surface of the pipe 108 at a predetermined interval. In this case, the transmission/reception unit 102 acquires the data of vibration from each of a plurality of the second detection units 105. Therefore, the transmission/reception unit 102 discriminates the second detection unit 105 transmitting the data of vibration and acquires the data. This operation can be realized by a conventional technology.

The vibration unit 107 applies the vibration (for example, a sound wave) with a plurality of frequency components to the pipe 108. The vibration applied to the pipe 108 is also transmitted to the fluid 110 flowing in the pipe 108. A piezoelectric vibration exciter, an electrodynamic vibration exciter, a mechanical vibration exciter, or the like can be used for the vibration unit 107. For attaching the vibration unit 107 on the outer surface of the pipe 108, for example, a magnet, a dedicated jig, or an adhesive material can be used.

The vibration applied by the vibration unit 107 propagates through the pipe 108 and the fluid 110 along a piping system. The vibration propagates in the horizontal direction of FIG. 1. However, when the leak part 109 exists in the pipe 108, a part of the vibration propagates to the outside of the pipe 108 through the leak part 109. By adjusting the amplitude of the vibration applied by the vibration unit 107, the vibration with a sufficiently large amplitude that propagates to the outside of the pipe 108 through the leak part 109 can reach the surface of the ground.

Further, the frequency of the vibration which easily propagates to the outside of the pipe 108 through the leak part 109 varies according to the size, the shape, or the like of the hole forming the leak part 109. Namely, a state in which the vibration with a first frequency easily propagates to the outside of the pipe 108 through a first leak part 109 but the vibration with a second frequency does not easily propagate to the outside of the pipe 108 through a first leak part 109 occurs. In this exemplary embodiment, because the vibration unit 107 applies the vibration with a plurality of frequency components, the vibration can easily propagate to the outside of the pipe through the leak part 109 independently of the size, the shape, or the like of the hole forming the leak part 109.

Figure 2:
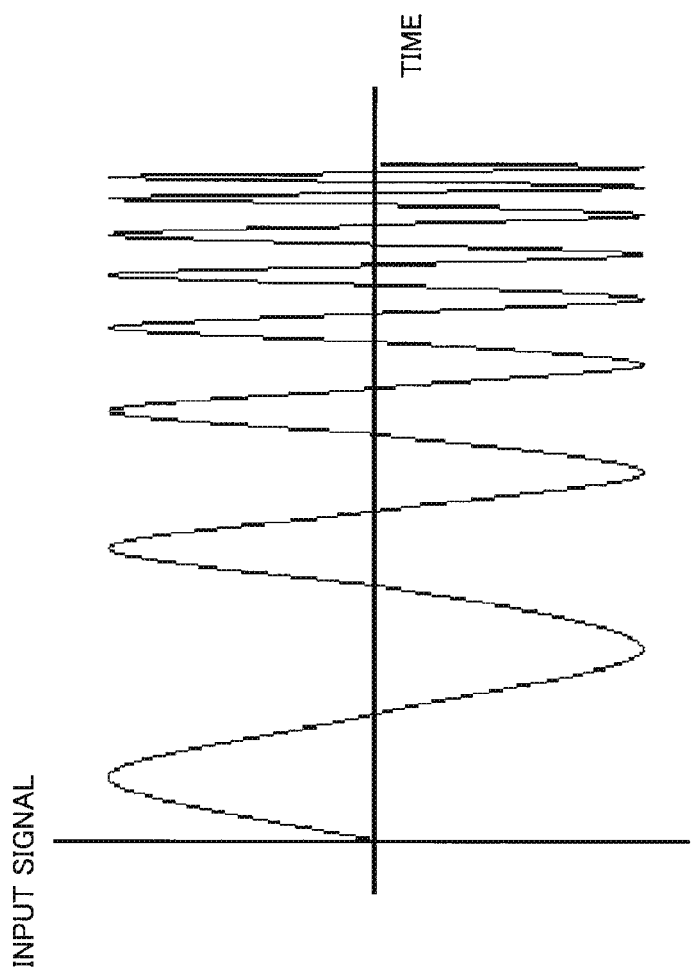
FIG. 2 is an example of a signal outputted from a vibration unit.

Further, means for applying the vibration with a plurality of frequency components is not limited in particular. The vibration with a plurality of frequency components may be applied or the vibration with one frequency component whose frequency can be changed may be applied while changing the frequency in turn. A signal having a wide frequency bandwidth is suitable for an inputted waveform. In FIG. 2, a frequency sweep signal whose frequency varies with time is shown as an example. For example, white noise, a pulse signal, or the like can also be used as the input signal.

The vibration unit 107 applies the above-mentioned vibration to the fluid 110 flowing in the pipe 108 in which the leak part 109 is detected. Namely, it is not necessary for the vibration unit 107 to apply the vibration at all times. After it is detected that the leak part 109 exists in the pipe 108, the vibration unit 107 can start to apply the vibration. For example, when a drive waveform is inputted from the processing device 100 described later, the vibration unit 107 can perform a process for applying the vibration according to the drive waveform.

The first detection unit 106 detects the vibration applied by the vibration unit 107. Specifically, the first detection unit 106 detects the vibration radiated to the outside of the pipe 108 through the leak part 109 in the vibration applied by the vibration unit 107. More specifically, the first detection unit 106 is installed on the surface of the ground and detects the vibration that is radiated to the outside of the pipe 108 and reaches the surface of the ground. Further, the first detection units 106 can be installed at a plurality of locations on the surface of the ground by changing the installation location and detect the vibration at each of a plurality of the installation locations.

As the first detection unit 106, for example, a sensor for measuring vibration of a solid can be used. A piezoelectric acceleration sensor, an electrodynamic acceleration sensor, a capacitance type acceleration sensor, an optical velocity sensor, a dynamic strain sensor, or the like can be used as the sensor for measuring vibration of a solid. The piezoelectric acceleration sensor is suitable for this purpose.

The first detection unit 106 transmits the measured data of vibration to the detection signal reception unit 103 of the processing device 100 described below.

Next, each unit included in the processing device 100 will be described.

The transmission/reception unit 102 has a function to receive the data (analog signal) of vibration measured by the second detection unit 105 from the second detection unit 105, a function to convert the received analog signal into a digital signal and transfer it to the signal processing unit 101, and a function to output the drive waveform to the vibration unit 107 according to the signal transferred from the signal processing unit 101. Specifically, the transmission/reception unit 102 has a signal amplification function, an analog-to-digital conversion function, and a digital-to-analog conversion function.

The detection signal reception unit 103 has a function to receive the data (analog signal) of vibration measured by the first detection unit 106 from the first detection unit 106 and a function to convert the received analog signal into the digital signal and transfer it to the signal processing unit 101. Specifically, the detection signal reception unit 103 has a signal amplification function and an analog-to-digital conversion function.

The signal processing unit 101 treats the signal (the data of vibration) measured by the second detection unit 105 at all times or intermittently (for example, one time a day, one time an hour, ten times every three minutes, or the like) and monitors whether or not the leak part 109 is formed in the pipe 108.

Further, the signal processing unit 101 treats the signal (the data of vibration) measured by each of a plurality of the second detection units 105 installed at a predetermined interval and specifies a coarse indication of the location of the leak part 109 formed in the pipe 108.

Further, the signal processing unit 101 treats the signal (the data of vibration) measured at each of a plurality of installation locations by the first detection unit 106 and specifies the location of the leak part 109 formed in the pipe 108.

Further, the signal processing unit 101 treats the signals (the data of vibration) measured by the first detection unit 106 and specifies the degree of the leak part 109 formed in the pipe 108. Specifically, the signal processing unit 101 extracts a feature amount from the vibration waveform measured by the first detection unit 106 and estimates the degree of the leak part 109 formed in the pipe 108 by using the extracted feature amount.

Figure 4:
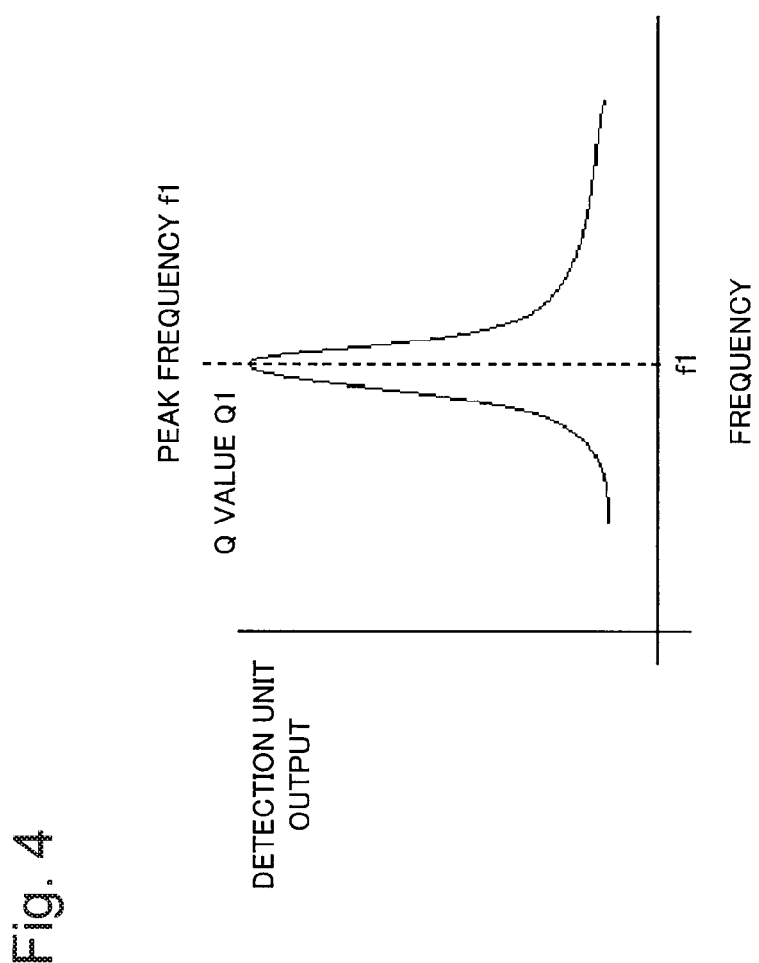
FIG. 4 shows an example of frequency response data obtained by an exemplary embodiment.

The signal processing unit 101 treats the signal (the data of vibration) measured by the first detection unit 106, extracts the amplitude as well as the frequency component of the vibration, and obtains frequency response data with at least one peak as shown in an example of FIG. 4. The signal processing unit 101 extracts either a peak frequency or a sharpness of the peak, preferably both as the feature amount.

Further, the signal processing unit 101 estimates at least one of the size of the hole formed in the pipe 108 and an amount of the fluid 110 flowing to the outside of the pipe 108 through the hole formed in the pipe 108 as the degree of the leak part 109 (defect) formed in the pipe 108.

Further, the signal processing unit 101 controls the signal (the drive waveform) inputted to the vibration unit 107.

Such signal processing unit 101 has a frequency analysis function, a threshold value determination function, and a filter function.

The reference data storage unit 104 stores data required for determining whether or not the leak part 109 exists, for calculating the size of the hole of the leak part 109, and for calculating a leakage amount. For example, data showing a feature of the vibration obtained when the water leak occurred in the past is stored.

For example, the reference data storage unit 104 may store reference data in which the feature amount extracted from the vibration waveform by the signal processing unit 101 is associated with the information (for example, the diameter of the hole) showing the degree of the leak part 109 formed in the pipe 108. Further, a relationship between the feature amount and the degree of the leak part 109 changes according to a structure (a thickness, a material, or the like) of the pipe 108 in which the leak part 109 is formed, an embedding environment (the soil density or the like), or the like. For this reason, the reference data storage unit 104 may store the reference data in which the above-mentioned feature amount is associated with the relationship between the feature amount and the degree of the leak part 109 for each condition.

The pipe information acquisition unit 115 acquires information about the pipe 108 located in the location in which the leak part 109 exists. For example, the pipe information acquisition unit 115 acquires information showing the structure (the thickness, the material, or the like) of the pipe 108 located in the location in which the leak part 109 exists and the embedding environment (the soil density or the like). Means for acquiring such information by the pipe information acquisition unit 115 is not limited in particular. For example, when the location of the leak part 109 is specified, a worker retrieves a material and specifies the above-mentioned information about the pipe 108 buried in the location in detail. Next, the worker inputs the specified information about the pipe 108 to the processing device 100. The pipe information acquisition unit 115 acquires the inputted information about the pipe 108 located in the location in which the leak part 109 exists.

These processes performed by the processing device 100 will be explained in detail below.

Figure 3:
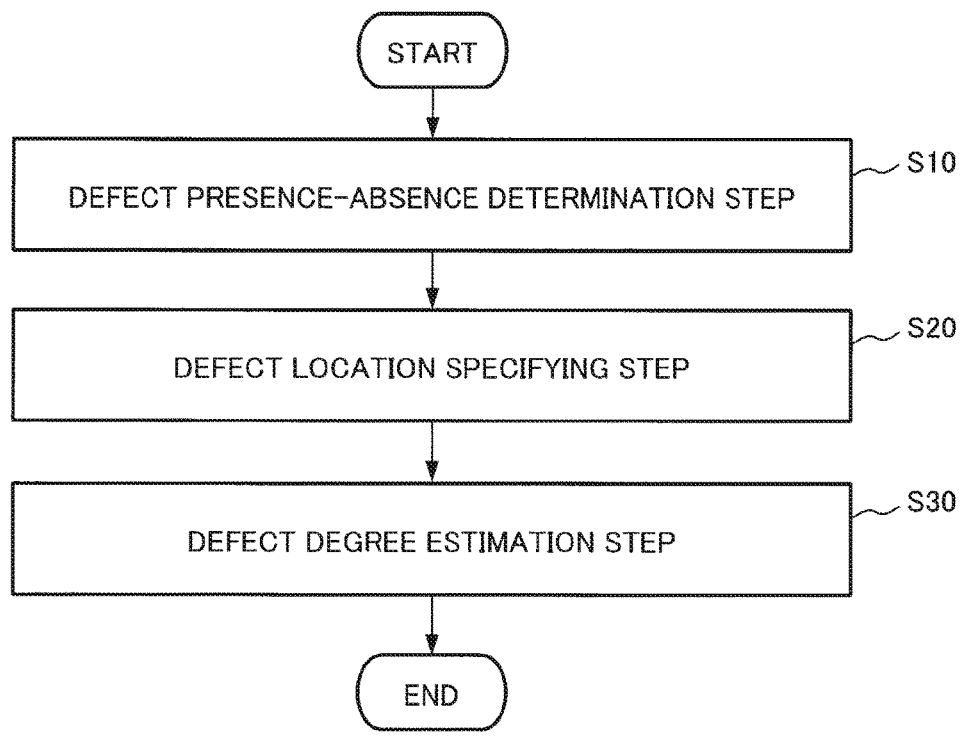
FIG. 3 is a flowchart showing an example of a process flow of a defect analysis method according to an exemplary embodiment.

Next, an example of a process flow of a defect analysis method performed by the defect analysis device according to the exemplary embodiment will be explained. FIG. 3 shows a flowchart showing an example of the process flow of the defect analysis method. As shown in FIG. 3, the defect analysis method according to the exemplary embodiment includes a defect presence-absence determination step S10, a defect location specifying step S20, and a defect degree estimation step S30.

In the defect presence-absence determination step S10, after the transmission/reception unit 102 receives the data of vibration measured by the second detection unit 105 and performs a predetermined process to the received data of vibration, the transmission/reception unit 102 transfers it to the signal processing unit 101. The signal processing unit 101 analyses the transferred data and determines whether or not the defect is formed in the pipe 108.

It is generally known that when the leak part 109 is formed in the pipe 108, the amplitude of the frequency component of the vibration in a certain frequency range is larger than that in a normal state. Namely, when the leak part 109 is formed in the pipe 108, a feature in which the amplitude of the frequency component of the vibration in a certain frequency range is larger than that in a normal state appears in the data of vibration measured by the second detection unit 105.

The signal processing unit 101 analyzes the data of vibration measured by the second detection unit 105 and determines whether or not this feature appears. Specifically, the signal processing unit 101 determines whether or not the amplitude exceeds a threshold value of the amplitude in the normal state and determines whether or not the leak part 109 is formed in the pipe 108.

Further, the above-mentioned threshold value varies according to the factors such as the material of the pipe 108, the diameter of the pipe 108, the buried environment, and the like. For this reason, the signal processing unit 101 holds the threshold value corresponding to each of these factors in advance. When the signal processing unit 101 receives the data of vibration from each of a plurality of the second detection units 105, the signal processing unit 101 may determine whether or not the leak part 109 is formed by using the threshold value corresponding to the factor in the installation location in which each of the second detection units 105 is installed. For example, in a case in which a plurality of the second detection units 105 are permanently installed on the pipe 108, the signal processing unit 101 may associate the above-mentioned threshold value with each of a plurality of the second detection units 105 and hold the threshold value in advance.

Alternatively, the signal processing unit 101 may calculate the above-mentioned threshold value for each of the second detection units 105 by using the data of vibration obtained in the normal state in the past that is acquired from each of a plurality of the second detection units 105. For example, the signal processing unit 101 may specify an upper limit value of the data of vibration in the normal state for each of the second detection units 105 and calculate the above-mentioned threshold value by using the specified upper limit value. The signal processing unit 101 may associate each second detection unit 105 or the location in which each second detection unit 105 is installed with the threshold value and output a determination result (whether or not the leak part 109 is formed) to the worker.

By this step, it can be detected by the signal processing unit 101 that the leak part 109 is formed in the pipe 108. Further, the signal processing unit 101 grasps the second detection unit 105 transmitting the data of vibration by which the leak part 109 is detected and whereby, the signal processing unit 101 can roughly specify the location (in the range in which the second detection unit 105 can detect the vibration) of the leak part 109.

In the defect presence-absence determination step S10, when it is determined by the signal processing unit 101 that the leak part 109 is formed in the pipe 108, the process advances to the defect location specifying step S20.

In the defect location specifying step S20, the location of the leak part 109 (defect) is specified. The step S20 may be composed of a first step in which the location of the leak part 109 is roughly specified (as a coarse indication) and a second step in which the location of the leak part 109 is precisely specified. Further, the process of the first step is not performed and only the process of the second step may be performed.

In the first step, the signal processing unit 101 specifies a coarse indication of the location of the leak part 109 by using the data of vibration measured by each of a plurality of the second detection units 105.

As mentioned above, a plurality of the second detection units 105 are installed at a predetermined interval. For this reason, the feature in which "the amplitude of the frequency component of the vibration in a certain frequency range is larger than that in a normal state" that appears when the leak part 109 is formed can be detected by a plurality of the second detection units 105. For example, the signal processing unit 101 may synchronize the data of vibration measured by each of a plurality of the second detection units 105, calculate a time difference between the times at which this feature is detected by a plurality of the second detection units 105, and specify the coarse indication of the location of the leak part 109 by using the time difference (correlation method).

In the second step, the vibration unit 107 applies the vibration with a plurality of frequency components to at least one of the fluid 110 flowing in the pipe 108 and the pipe 108. In a state in which the vibration is applied, the installation location of the first detection unit 106 on the surface of the ground is changed (the first detection unit 106 is moved) and the vibration is measured by the first detection unit 106 at each of a plurality of the installation locations. Further, because the coarse indication of the location of the leak part 109 is specified in the first step, the vibration can be measured in the location specified as the coarse indication while changing the installation location of the first detection unit 106. The signal processing unit 101 treats the data of vibration measured at each of a plurality of the installation locations by the first detection unit 106 and specifies the location of the leak part 109.

Thus, when it is detected by the signal processing unit 101 that the leak part 109 is formed in the pipe 108, the vibration unit 107 can start to apply the vibration to at least one of the fluid 110 and the pipe 108. The first detection unit 106 detects the vibration applied by the vibration unit 107. For example, when it is detected by the signal processing unit 101 that the leak part 109 is formed in the pipe 108, the vibration unit 107 may use it as a trigger and start to apply the vibration. Alternatively, when the worker acquires information indicating that the leak part 109 is formed, the worker inputs an instruction which causes the vibration unit 107 to start to apply the vibration and then, the vibration unit 107 may use it as the trigger and start to apply the vibration. When such configuration is used, the vibration is prevented from being unnecessarily applied by the vibration unit 107 and the detection process by the first detection unit 106 can be suppressed and whereby, the power consumed by these processes can be reduced.

When the vibration (refer to for example, FIG. 2) applied by the vibration unit 107 propagates through the pipe 108 and the fluid 110, a part of the vibration is transmitted to the outside of the pipe 108 through the leak part 109 and reaches the surface of the ground. The vibration which reaches the surface of the ground is measured by the first detection unit 106. After the measurement, in the signal processing unit 101, the amplitude as well as the frequency component of the vibration are extracted and the frequency response data with at least one peak as shown in an example of FIG. 4 is obtained. The frequency of the peak and the sharpness of the peak mainly depend on the size of the hole of the leak part 109 and further depend on the structure (the thickness, the material, or the like) of the pipe 108 and the embedding environment (the soil density or the like).

The signal processing unit 101 performs a comparison process in which the comparison of the data of vibration that are measured at a plurality of the installation locations by the first detection unit 106 is performed, determines the location in which the output level of the peak is maximum, and regards this location as the location just above the leak part 109.

Further, in the second step, without using the signal processing unit 101 to specify the location of the leak part 109, the worker can specify the location of the leak part 109 based on the frequency response data shown in FIG. 4. For example, a method of which the first detection unit 106 is moved (automatically moved or manually moved by the worker) on the surface of the ground, the vibration is measured in each location by the first detection unit 106, and the frequency response data (refer to FIG. 4) obtained by processing the measured data of vibration is displayed on a display in real time can be used. The worker may move the first detection unit 106 on the surface of the ground, confirm the frequency response data displayed on the display, and specify the installation location of the first detection unit 106 at which the output level of the peak is maximum.

Alternatively, without moving the first detection unit 106 on the surface of the ground, a method of which a plurality of the first detection units 106 are installed at a predetermined interval on the surface of the ground, the vibration is measured by each of a plurality of the first detection units 106, and it is determined that the installation location of the first detection unit 106 at which the output level of the signal is maximum is just above the leak part 109 may be used.

Returning to FIG. 3, in the defect degree estimation step S30, the vibration unit 107 applies the vibration with a plurality of frequency components to the pipe 108. The vibration applied to the pipe 108 is also transmitted to the fluid 110 flowing in the pipe 108. The vibration propagates through the pipe 108 and the fluid 110 in the pipe 108. The first detection unit 106 measures the vibration in a state in which the vibration is applied. Namely, the first detection unit 106 measures the vibration applied by the vibration unit 107. For example, the first detection unit 106 is installed in the location on the surface of the ground that is just above the leak part 109 specified in the defect location specifying step S20. The signal processing unit 101 treats the data of vibration measured by the first detection unit 106 and estimates the degree of the leak part 109.

As explained by using FIG. 4, the frequency and the shape of the peak in the above-mentioned frequency response data mainly depend on the size of the hole of the leak part 109 and also may depend on the structure (the thickness, the material, or the like) of the pipe 108 and the embedding environment (the soil density or the like). Namely, this means that this frequency response data can be used as an index indicating the size of the hole of the leak part 109 and the leakage amount.

Figure 5:
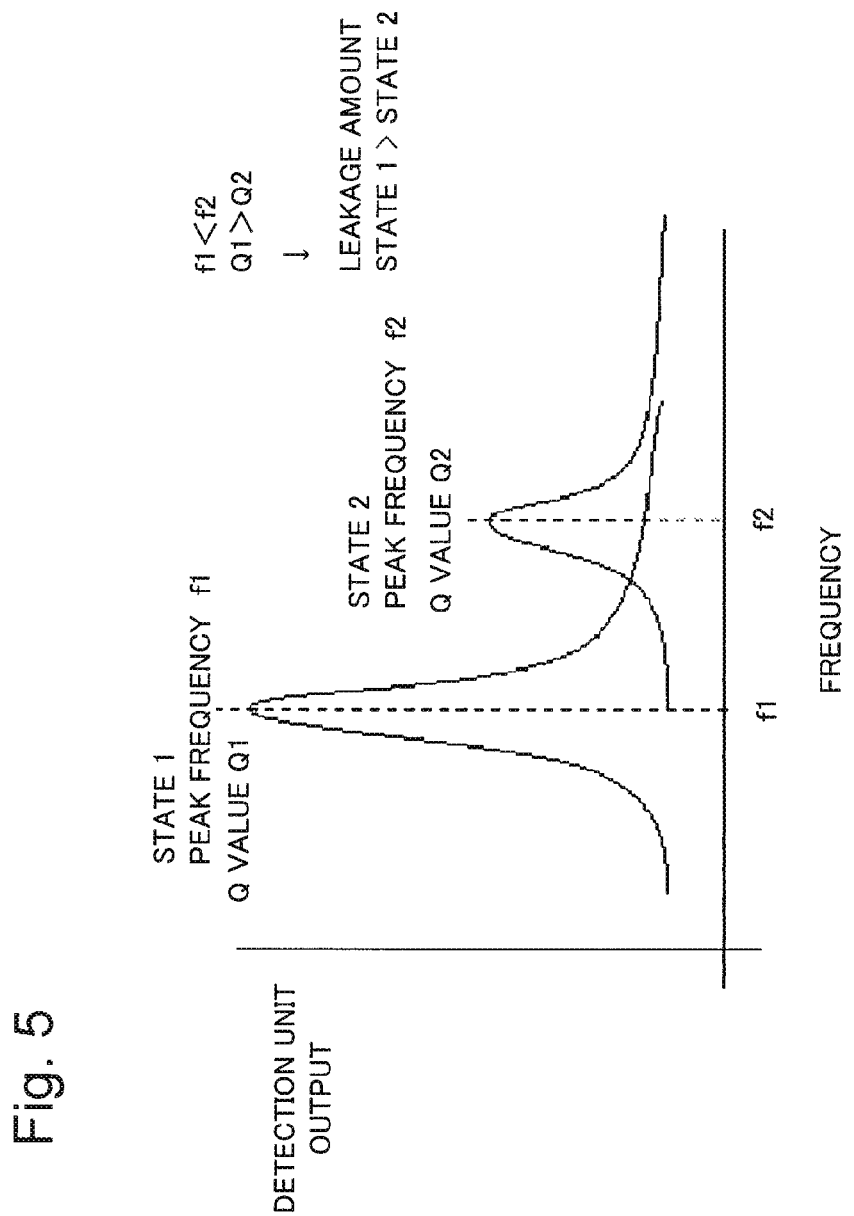
FIG. 5 is a figure for explaining an effect on operation of an exemplary embodiment.

FIG. 5 is an outline drawing showing a principle. As shown in FIG. 5, when there are two leak parts 109 of which the sizes of the leak parts 109 are different from each other, the frequency response data including two peaks whose frequencies and sharpness Q are different from each other is obtained from the measurement. The feature amount and the size (the leak amount) of the hole of the leak part 109 have a predetermined relation to each other. Specifically, as shown in FIG. 5, when the value of the peak frequency becomes small, the size of the hole of the leak part 109 becomes large. Further, when the value of the sharpness Q of the peak becomes large, the size of the hole of the leak part 109 becomes large. For this reason, when the reference data in which the size of the hole of the leak part 109 is associated with the feature amount (either the peak frequency or the sharpness or preferably both) extracted from the frequency response data is stored in the reference data storage unit 104, the size of the hole of the leak part 109 can be specified by using the data of vibration measured by the first detection unit 106.

Further, the relation between the size of the hole of the leak part 109 and the feature amount (either the peak frequency or the sharpness or preferably both) extracted from the frequency response data may depend on the structure (the thickness, the material, or the like) of the pipe 108 in which the leak part 109 exists and the embedding environment (the soil density or the like). For this reason, it is desirable to store the reference data in which the size of the hole of the leak part 109 is associated with the feature amount (either the peak frequency or the sharpness or preferably both) extracted from the frequency response data for each structure (the thickness, the material, or the like) of the pipe 108 or each embedding environment (the soil density or the like) in the reference data storage unit 104.

Here, an example of the reference data is shown in FIGS. 12 to 14. In an example shown in FIG. 12, the size of the hole of the leak part 109 is associated with the peak frequency that is the feature amount extracted from the frequency response data for each thickness of the pipe 108. In an example shown in FIG. 13, the size of the hole of the leak part 109 is associated with the sharpness of the peak that is the feature amount extracted from the frequency response data for each thickness of the pipe 108. In an example shown in FIG. 14, the size of the hole of the leak part 109 is associated with the peak frequency that is the feature amount extracted from the frequency response data for each of the combinations of a plurality of information about the thickness, the material, and the like of the pipe 108.

In this step, the signal processing unit 101 treats the data of vibration measured by the first detection unit 106, obtains the frequency response data as shown in an example of FIG. 4, and calculates either the peak frequency or the sharpness of the peak, or preferably both.

In this step, the pipe information acquisition unit 115 receives the information (the structure (the thickness, the material, or the like) of the pipe 108, the embedding environment (the soil density or the like) around the location in which the leak part 109 of the pipe 108 exists, or the like) inputted by the worker. For example, when the location of the leak part 109 is specified in the defect location specifying step S20, the worker retrieves the predetermined material and specifies the information (the structure (the thickness, the material, or the like) of the pipe 108, the embedding environment (the soil density or the like) around the location in which the leak part 109 of the pipe 108 exists or the like). After this process, the worker inputs the specified information about the pipe 108 to the processing device 100. The pipe information acquisition unit 115 acquires the information about the pipe 108 (the structure (the thickness, the material, or the like) of the pipe 108, the embedding environment (the soil density or the like), or the like) inputted in such a manner.

The signal processing unit 101 retrieves the reference data (refer to FIGS. 12 to 14) by using the information about the pipe 108 (the structure (the thickness, the material, or the like) of the pipe 108, the embedding environment (the soil density or the like), or the like) acquired by the pipe information acquisition unit 115 as a key and specifies the reference data corresponding to the information about the pipe 108. After this process, the signal processing unit 101 retrieves the specified reference data by using either the calculated peak frequency or the calculated sharpness or preferably both as the key and specifies the size of the hole. When the calculated peak frequency and the calculated sharpness are used as the key, the signal processing unit 101 retrieves the reference data by using the calculated peak frequency and the calculated sharpness as the key in turn and specifies the size of the hole. For example, when the size of the hole which is specified by using the peak frequency as the key is not equal to the size of the hole which is specified by using the sharpness as the key, the signal processing unit 101 may output the size of the hole that is larger than the other as a result.

Further, when the size of the hole can be specified, the leak amount of the fluid 110 can be calculated by using the size of the hole and the pressure applied by a pump so that the fluid 110 flows in the pipe 108.

In the exemplary embodiment, the vibration is intentionally applied by the vibration unit 107. Therefore, the timing of pressure application and the frequency component can be grasped. Namely, the vibration can be easily distinguished from a disturbance component.

By using the exemplary embodiment mentioned above, determination of whether the leak part 109 (defect) is formed, determination of the location of the leak part 109 (defect), and estimation of the degree of the leak part 109 (defect) can be performed without using the check by ear of the skilled checker.

Further, as described above, in the exemplary embodiment, the vibration applied by the vibration unit 107 is detected by the first detection unit 106. The signal processing unit 101 extracts the feature amount from the vibration waveform acquired by the first detection unit 106 and estimates the degree of the leak part 109 (defect) formed in the pipe 108 by using the extracted feature amount.

Namely, in the exemplary embodiment, the vibration is applied to the fluid 110 and the pipe 108, the vibration propagates through the fluid 110 and the pipe 108, this vibration is detected and analyzed, and whereby, the degree of the leak part 109 (defect) is estimated. Therefore, the vibration with a sufficiently large amplitude can be detected and based on this detection result, the degree of the leak part 109 (defect) can be estimated with a high degree of accuracy.

Further, in the exemplary embodiment, the vibration unit 107 applies the vibration with a plurality of frequency components. As mentioned above, the easiness of transmission of the vibration to the outside of the pipe 108 through the leak part 109 (defect) depends on the frequency of the vibration. When this exemplary embodiment is used, because the vibration with a plurality of frequency components is applied, the vibration can easily propagate to the outside of the pipe 108 through the leak part 109 (defect). Therefore, the first detection unit 106 can detect the vibration with a sufficiently large amplitude that is transmitted to the outside of the pipe 108 through the leak part 109 (defect). As a result, the degree of the leak part 109 (defect) can be estimated with a high degree of accuracy.

(Second Exemplary Embodiment)

Figure 6:
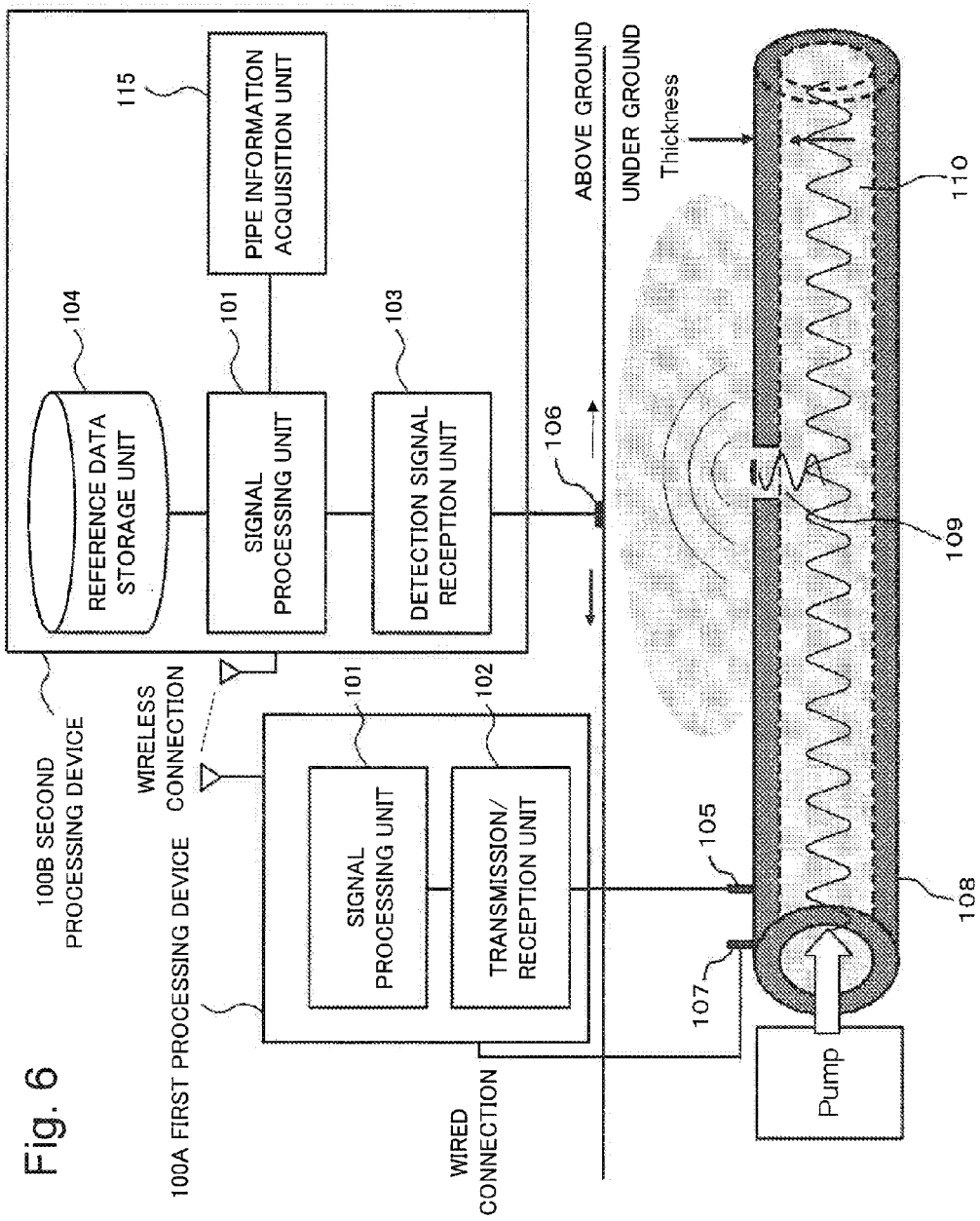
FIG. 6 is an example of a conceptual rendering of a defect analysis device according to an exemplary embodiment.

FIG. 6 shows an example of a conceptual rendering of a defect analysis device according to a second exemplary embodiment.

The present exemplary embodiment is different from the first exemplary embodiment in view of a point such that a processing device 100, explained in first the exemplary embodiment, is composed of a first processing device 100A and a second processing device 100B physically separated each other. The configuration of the second exemplary embodiment other than this difference can be made the same as the configuration of the first exemplary embodiment. Therefore, the description will be omitted.

The first processing device 100A includes a signal processing unit 101 and a transmission/reception unit 102. The second processing device 100B includes a signal processing unit 101, a detection signal reception unit 103, a reference data storage unit 104, and a pipe information acquisition unit 115. The first processing device 100A and the second processing device 100B are configured so as to be communicable to each other through a wireless connection. Further, the first processing device 100A and the second processing device 100B may be configured so as to be communicable to each other through a wired connection.

By using this exemplary embodiment, even when the vibration unit 107 is located far from the first detection unit 106, the location of the leak part 109 can be specified and the degree of the leak part 109 can be estimated without difficulty.

(Third Exemplary Embodiment)

Figure 7:
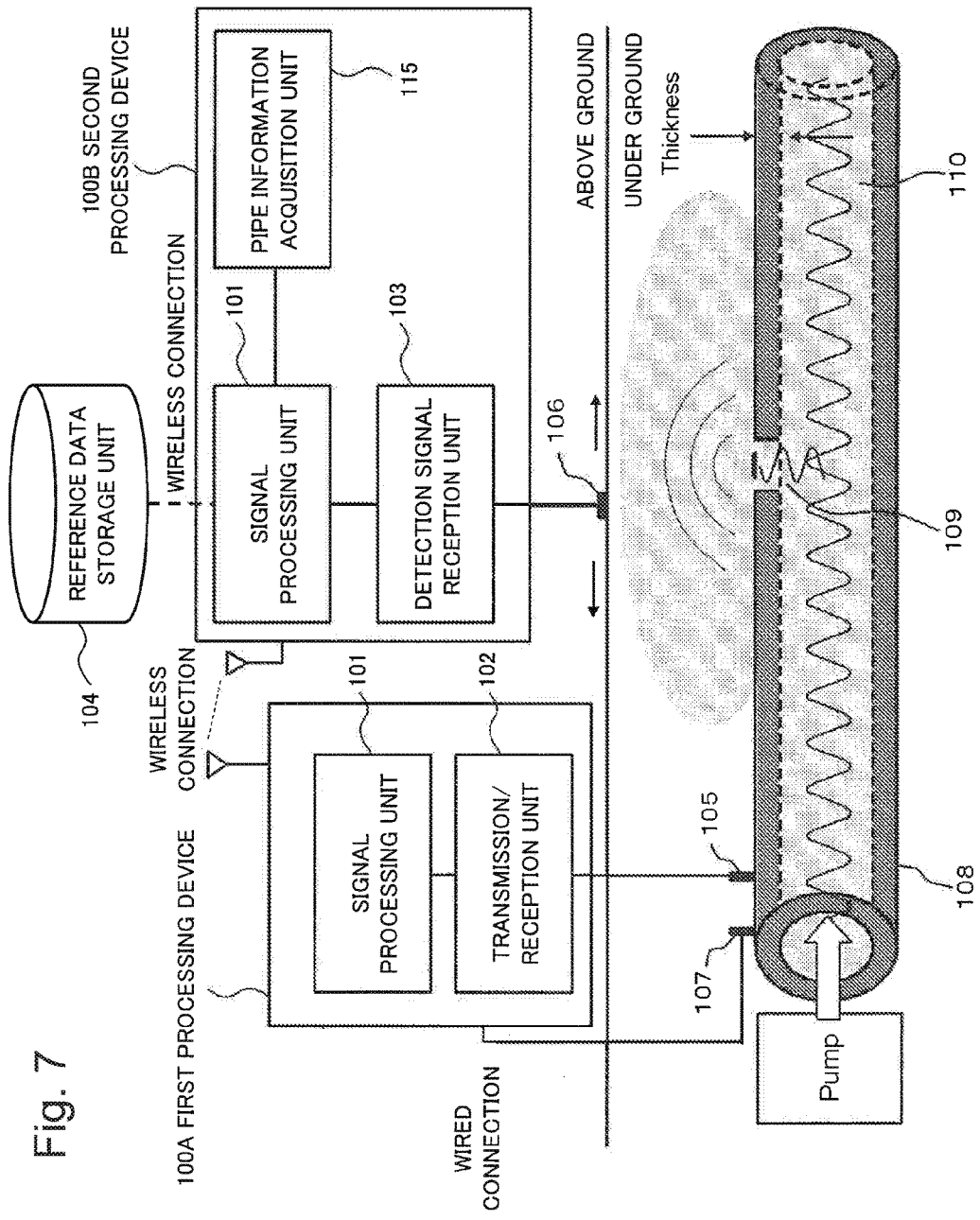
FIG. 7 is an example of a conceptual rendering of a defect analysis device according to an exemplary embodiment.

FIG. 7 shows an example of a conceptual rendering of a defect analysis device according to a third exemplary embodiment.

This exemplary embodiment is configured on the basis of the configuration of the second exemplary embodiment, and is different from that in view of point such that the reference data storage unit 104 is separately provided from the second processing device 100B. The configuration of the third exemplary embodiment other than this difference can be made the same as the configuration of the second exemplary embodiment. Therefore, the description will be omitted.

The reference data storage unit 104 and the second processing device 100B are configured so as to be communicable to each other through a wireless connection. Further, the reference data storage unit 104 and the second processing device 100B may be configured so as to be communicable to each other through a wired connection. For example, the reference data storage unit 104 is included in a server or the like on a network and the second processing device 100B accesses such reference data storage unit 104 and refers to the predetermined data.

This exemplary embodiment has an advantageous effect in which data can be integrally managed and an analysis that needs a lot of reference data which cannot be stored in the device can be performed.

(Fourth Exemplary Embodiment)

Figure 8:
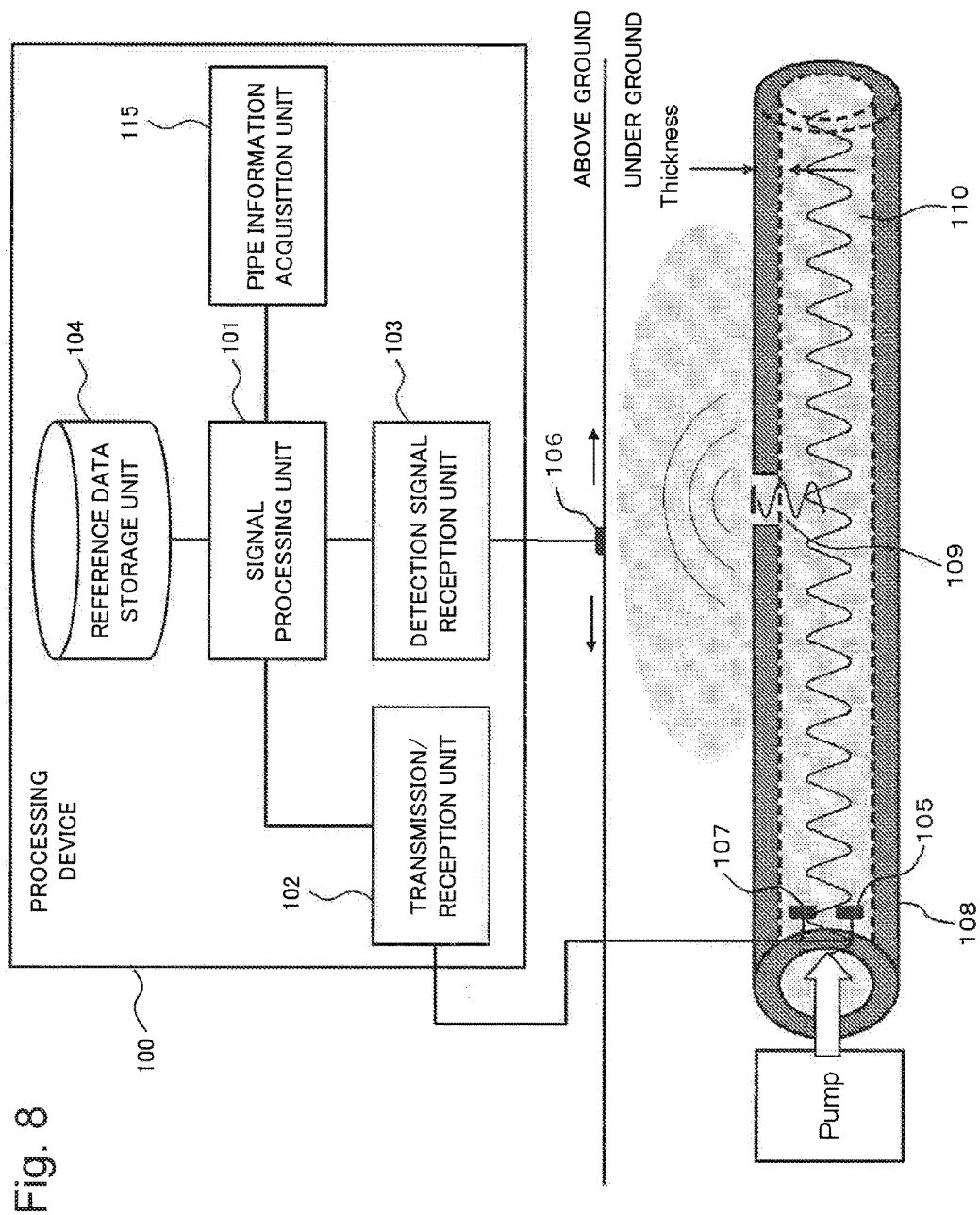
FIG. 8 is an example of a conceptual rendering of a defect analysis device according to an exemplary embodiment.

FIG. 8 shows an example of a conceptual rendering of a defect analysis device according to a fourth exemplary embodiment.

The present exemplary embodiment is different from the first to third exemplary embodiments in view of point such that the second detection unit 105 and the vibration unit 107 are installed inside the pipe 108. The configuration of the fourth exemplary embodiment other than this difference can be made the same as the configuration of the first to third exemplary embodiments. Therefore, the description will be omitted.

By using this exemplary embodiment, it is possible to directly apply the vibration to the fluid 110 and directly detect the vibration propagating through the fluid 110. In the fourth exemplary embodiment, it is necessary to insert the structural objects (the second detection unit 105 and the vibration unit 107) inside the pipe 108 unlike the first to third exemplary embodiments. Therefore, the second detection unit 105 and the vibration unit 107 cannot be easily installed. However, because the vibration in the fluid 110 that is less attenuated with distance can be directly treated, the fourth exemplary embodiment is useful when the leak part 109 is located far from the second detection unit 105.

(Fifth Exemplary Embodiment)

Figure 9:
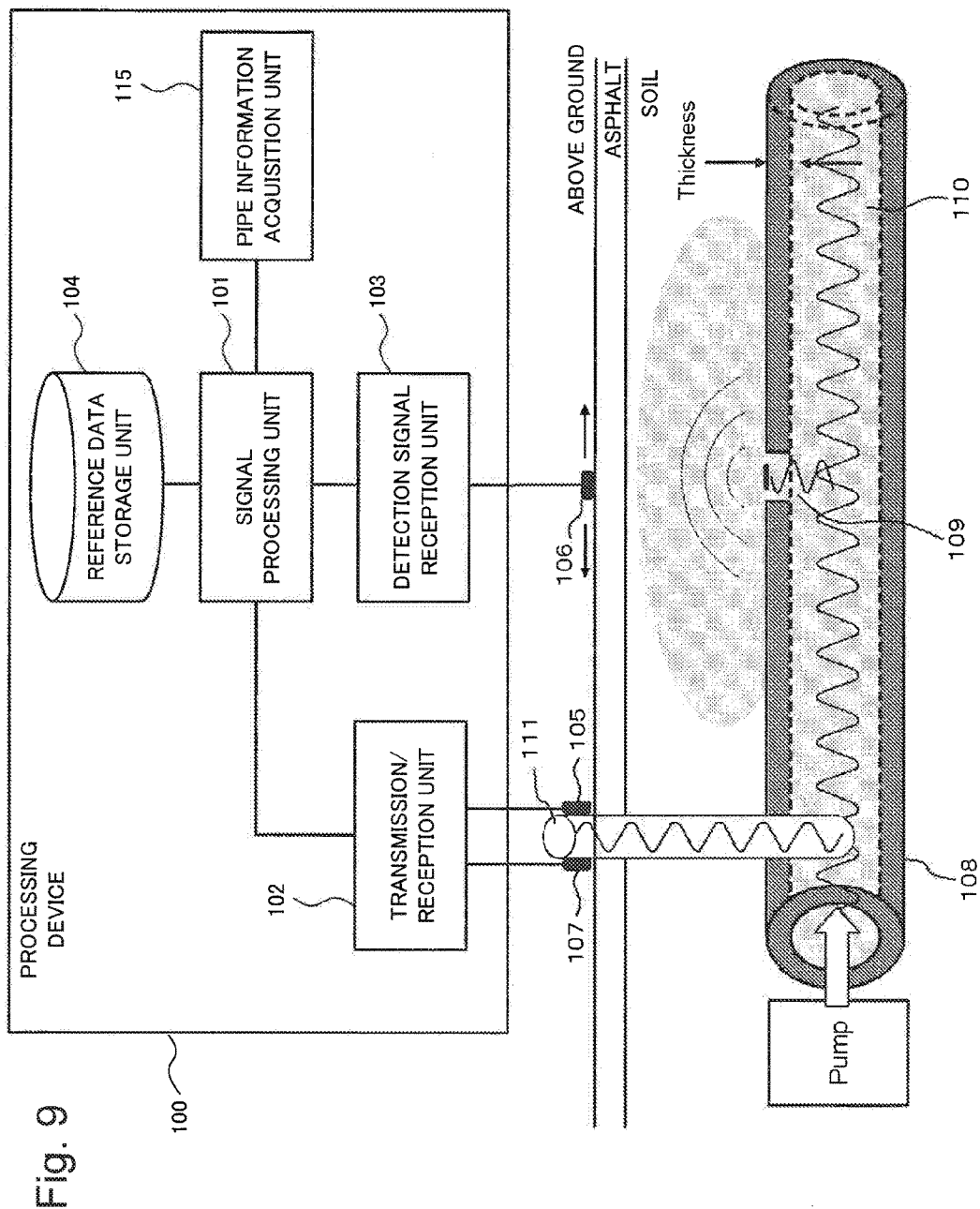
FIG. 9 is an example of a conceptual rendering of a defect analysis device according to an exemplary embodiment.

FIG. 9 shows an example of a conceptual rendering of a defect analysis device according to a second exemplary embodiment.

The present exemplary embodiment is different from the first to fourth exemplary embodiments in view of point such that the second detection unit 105 and the vibration unit 107 are installed on the outer surface of a branch pipe 111 connected to the pipe 108. The branch pipe 111 is a pipe connected to the pipe 108 that is an object of defect detection. For example, the exemplary embodiment may be applied to a case shown in FIG. 9 in which asphalt exists on the surface of the ground and the branch pipe 111 is a manhole. In this case, the second detection unit 105 and the vibration unit 107 may be installed on the inner surface of the manhole that is the branch pipe 111. The configuration of the fifth exemplary embodiment other than this difference can be made the same as the configuration of the first to fourth exemplary embodiments. Therefore, the description will be omitted.

When this exemplary embodiment is used, the vibration unit 107 and the second detection unit 105 can be very easily installed. Therefore, this exemplary embodiment has an advantageous effect in which the labor and time required for the check work can be reduced.

In the exemplary embodiment described above, a case in which the fluid flowing in the pipe 108 is liquid has been explained as an example. However, the fluid may be gas. In the exemplary embodiments described above, a case in which the pipe 108 is installed under the ground has been explained as an example. However, the pipe 108 may be installed in an attic or a basement of a building or may be buried in a wall or a pillar. In this case, the first detection unit 106 can be installed on a ceiling surface, a wall surface, a side surface of the pillar, a floor surface, or the like.

EXAMPLE

A result of verification performed to verify availability of the above-mentioned exemplary embodiment will be described below.

Figure 10:
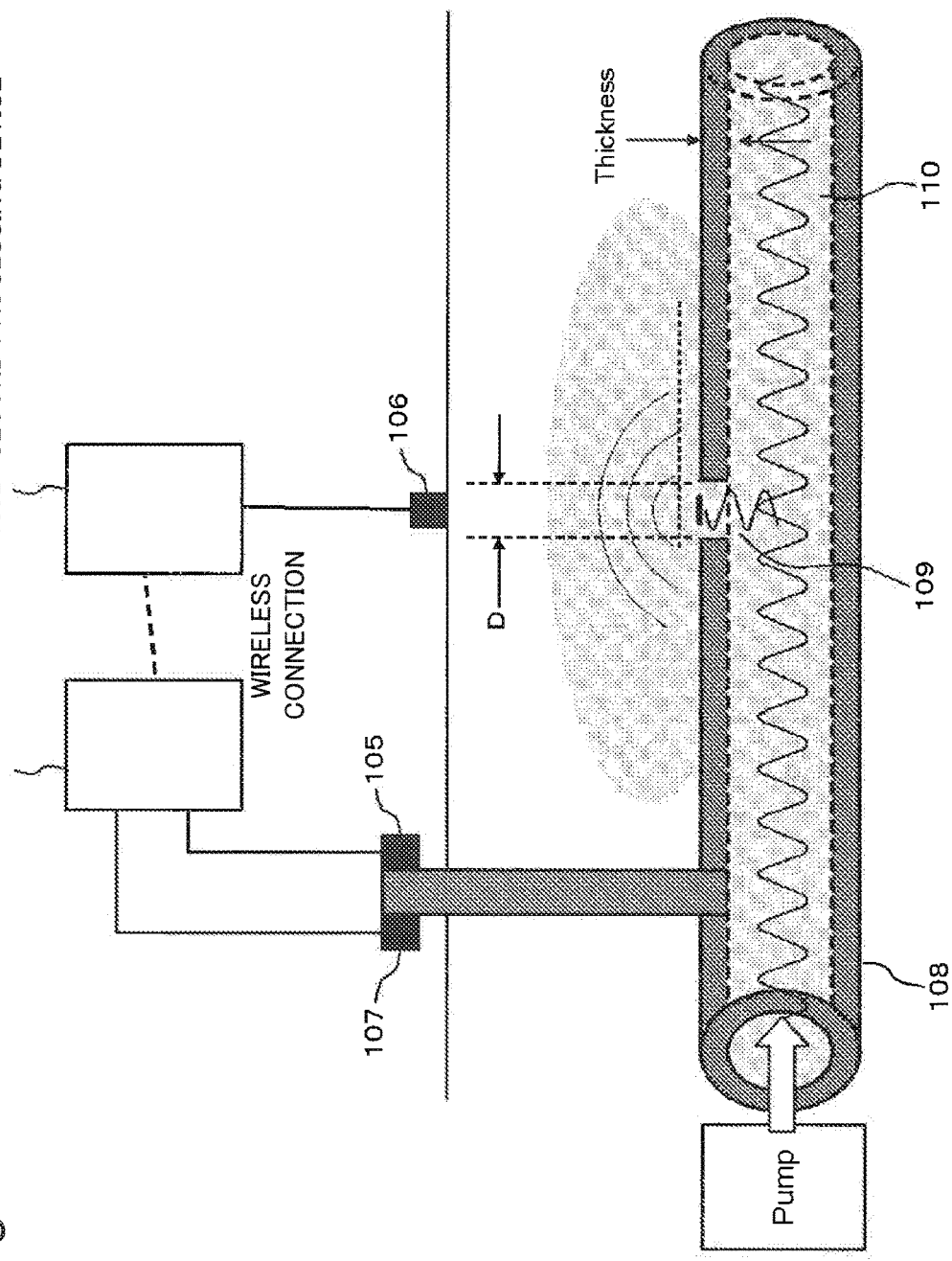
FIG. 10 is a figure for explaining a configuration of a defect analysis device of an example.

FIG. 10 is a figure schematically showing a configuration of this example. In order to simulate water leak from a water pipe, a metal pipe 108 filled with water is prepared and buried under the ground. The branch pipe is connected to the pipe 108. A second detection unit 105 and a vibration unit 107 are installed on the outer surface of this branch pipe. A pump for sending water is connected to the left end of the pipe 108 and operated. The hole for simulating a leak part 109 is provided on the way of the pipe 108. Water leaks to the outside of the pipe 108 through this hole.

In this state, the data of vibration is measured by the second detection unit 105. The feature in which the amplitude of the vibration with the frequency component in a certain range is larger than that in a normal state is observed. This phenomenon is caused by existence of the leak part 109. Further, the measurement is repeated under different conditions under which the pipe wall thickness and the size of the hole of the leak part 109 are changed and the above-mentioned feature is observed in all the conditions. Namely, by using this exemplary embodiment, the leak part 109 of the pipe 108 can be detected. This is confirmed by the measurement result.

Next, the vibration with a sweep frequency is applied to the branch pipe by the vibration unit 107 and in this state, the vibration radiated to the outside of the pipe 108 through the leak part 109 is measured by the first detection unit 106 installed on the surface of the ground.

When the first detection unit 106 installed on the surface of the ground is moved by hand, the measured amplitude of the vibration varies according to the location of the first detection unit 106. The measurement result shows that the location in which the measured amplitude of the vibration is maximum is a location just above the leak part 109. Namely, by using this exemplary embodiment, the location of the leak part 109 of the pipe 108 can be specified. This is confirmed by the measurement result.

Next, a frequency analysis of the data of vibration acquired by the first detection unit 106 is performed by the signal processing unit 101 provided in the second processing device 100B and then, the peak frequency and the value of the sharpness Q are extracted.

Figure 11:
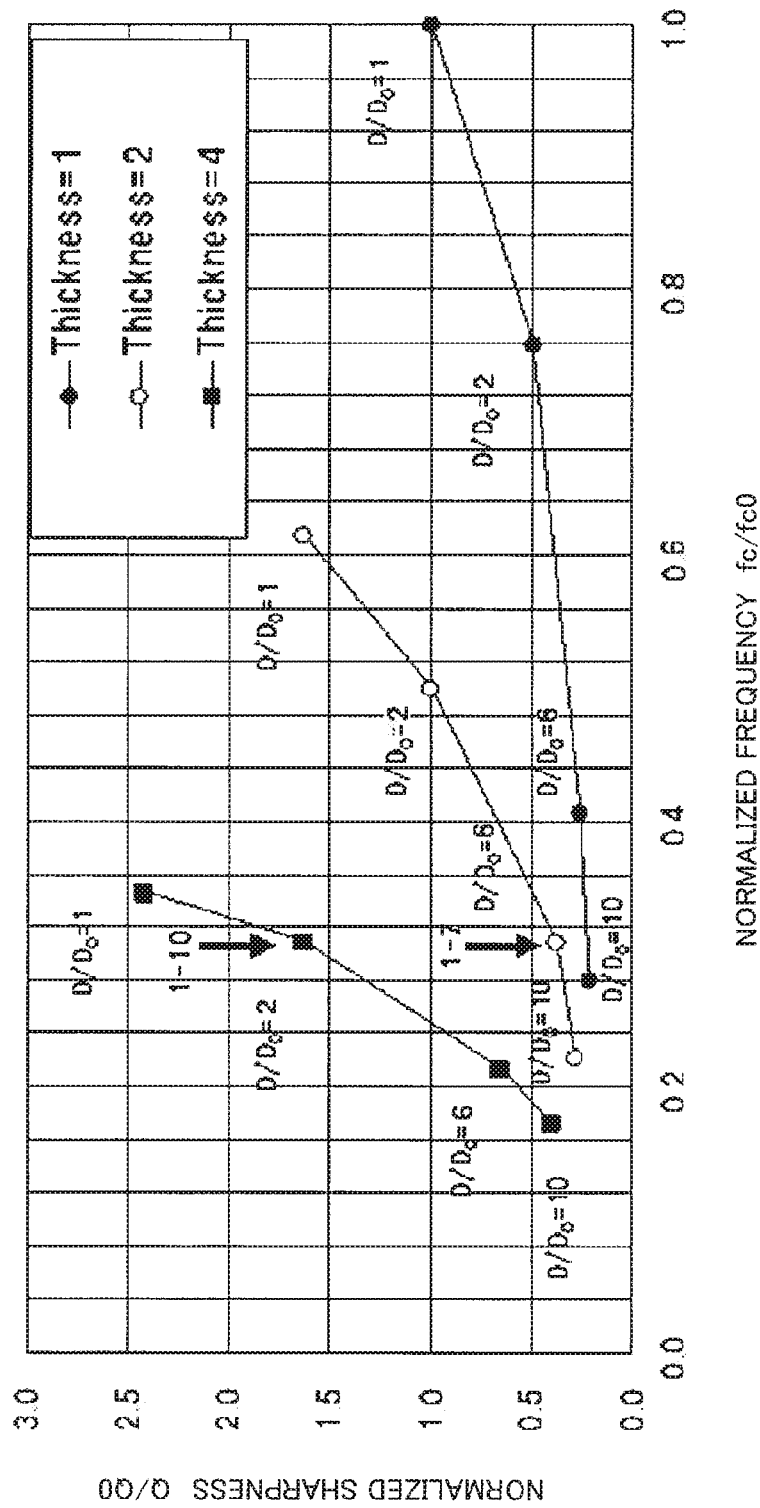
FIG. 11 is a figure for explaining a result of an example.

Similarly, the measurement is repeated under different conditions under which the pipe wall thickness of the pipe 108 and the size of the hole of the leak part 109 are changed. After the measurement, a plurality of measurement data are normalized so that the peak frequency, the sharpness Q, the pipe wall thickness, the diameter of the leak part, and the leakage amount in a condition in which the thickness of the pipe 108 is 5 mm and the diameter of the leak part 109 (the hole) is 5 mm are unity. The normalized value is shown in table 1 and FIG. 11.

From this result, it is clear that the peak frequency and the sharpness systematically vary according to the change in the pipe wall thickness of the pipe 108 and the change in the diameter of the leak part 109.

Here, it is verified whether the peak frequency and the sharpness can be used as the index of water leak or not. As an example, we focus on two points (No. 1-7 and No. 1-10) indicated by the arrows in FIG. 11: one is a point (No. 1-10) at which the normalized pipe wall thickness is 4 and the normalized diameter of the leak part is 2 and the other is a point (No. 1-7) at which the normalized pipe wall thickness is 2 and the normalized diameter of the leak part is 6 are examined.

Two of the normalized leakage amounts at these two points are compared with each other. The normalized leakage amount at the point (No. 1-10) is 4 and the normalized leakage amount at the point (No. 1-7) is 36. When only the peak frequency is used as the index, the values of the peak frequencies at two points are very close to each other and it is difficult to distinguish them from each other. Namely, it shows that when the water leak occurs, there is a possibility that an erroneous determination is made for urgency. On the other hand, when the peak frequency and the sharpness Q of the peak are used as the index, it is easy to distinguish two states as clearly shown in FIG. 11 and table 1.

TABLE 1

| NO. | NORMALIZED FREQUENCY | NORMALIZED SHARPNESS | NORMALIZED DIAMETER | NORMALIZED THICKNESS | NORMALIZED LEAKAGE AMOUNT |
|---|---|---|---|---|---|
| 1-1 | 1.00 | 1.00 | 1 | 1 | 1 |
| 1-2 | 0.76 | 0.49 | 2 | 1 | 4 |
| 1-3 | 0.41 | 0.26 | 6 | 1 | 36 |
| 1-4 | 0.28 | 0.21 | 10 | 1 | 100 |
| 1-5 | 0.62 | 1.63 | 1 | 2 | 1 |
| 1-6 | 0.50 | 1.00 | 2 | 2 | 4 |
| 1-7 | 0.31 | 0.37 | 6 | 2 | 36 |
| 1-8 | 0.22 | 0.28 | 10 | 2 | 100 |
| 1-9 | 0.35 | 2.42 | 1 | 4 | 1 |
| 1-10 | 0.31 | 1.63 | 2 | 4 | 4 |
| 1-11 | 0.21 | 0.65 | 6 | 4 | 36 |
| 1-12 | 0.17 | 0.39 | 10 | 4 | 100 |

The reference data related to the structure (the thickness, the material, or the like) of the pipe 108, the embedding environment (the soil density or the like), or the like is stored in the reference data storage unit 104 and the measurement result is compared with the reference data. Whereby, the size of the hole of the leak part 109 and the leakage amount can be easily calculated. In a series of measurements, the measurement has been performed without being affected by a car noise and a disturbance.

It has been shown above that determination of whether the leak part 109 (defect) is formed, determination of the location of the leak part 109 (defect), and estimation of the degree of the leak part 109 (defect) can be performed without using the check by ear of the skilled checker.

<<Supplementary Note>>

By the above-mentioned description, the following invention has been explained.

<Invention 1>

A defect analysis device including:

vibration means for applying vibration with a plurality of frequency components to at least one of fluid flowing in a pipe and the pipe, first detection means for detecting the vibration applied by the vibration means, and signal processing means for extracting a feature amount from a vibration waveform acquired by the first detection means and estimate a degree of defect formed in the pipe by using the extracted feature amount.

<Invention 2>

The defect analysis device described in invention 1, wherein the signal processing means extract at least one of a peak frequency and a sharpness of a peak as the feature amount.

<Invention 3>

The defect analysis device described in invention 1 or invention 2, wherein the signal processing means estimate at least one of a size of a hole formed in the pipe and an amount of fluid which leaks to the outside of the pipe through the hole formed in the pipe as the degree of defect formed in the pipe.

<Invention 4>

The defect analysis device described in any one of inventions 1 to 3, wherein the defect analysis device further includes reference data storage means for storing reference data in which the feature amount is associated with information indicating the degree of defect formed in the pipe and the signal processing means retrieve the reference data by using the feature amount as a key and estimate the degree of defect formed in the pipe.

<Invention 5>

The defect analysis device described in invention 4, wherein the defect analysis device further includes pipe information acquisition means for acquiring information about the pipe in which defect exists, the reference data storage mean store the reference data for each of the information about the pipe, and the signal processing means specify the reference data to be retrieved by using the information about the pipe acquired by the pipe information acquisition means and retrieve the specified reference data by using the feature amount as the key.

<Invention 6>

The defect analysis device described in any one of inventions 1 to 5, wherein the vibration means apply vibration to at least one of the fluid flowing in the pipe in which defect is detected and the pipe and the first detection means detect the vibration radiated to the outside of the pipe through the defect.

<Invention 7>

The defect analysis device described in any one of inventions 1 to 6, wherein the vibration means are installed on the outer surface of the pipe or the outer surface of a branch pipe connected to the pipe.

<Invention 8>

The defect analysis device described in any one of inventions 1 to 7, wherein the pipe is installed under the ground and the first detection means are installed on the surface of the ground and detect the vibration that is radiated to the outside of the pipe and reaches the surface of the ground.

<Invention 9>

The defect analysis device described in invention 8, wherein the first detection means can be moved to a plurality of different locations on the surface of the ground and detect the vibration at each of a plurality of the installation locations and the signal processing means use a plurality of vibration waveforms acquired at each of a plurality of the installation locations by the first detection means and specify the location of the defect formed in the pipe.

<Invention 10>

The defect analysis device described in any one of inventions 1 to 9, wherein the defect analysis device further includes second detection means for detecting at least one of the vibration propagating through the pipe and the vibration propagating through the fluid flowing in the pipe and the signal processing means detect the formation of defect in the pipe by using the vibration detected by the second detection means.

<Invention 11>

The defect analysis device described in invention 10, wherein the second detection means are installed on the outer surface of the pipe or the outer surface of the branch pipe connected to the pipe.

<Invention 12>

The defect analysis device described in invention 10 or invention 11, wherein the defect analysis device includes a plurality of the second detection means and a plurality of the second detection means are installed at a predetermined interval and the signal processing means specify a coarse indication of the location of the defect formed in the pipe by using the vibration detected by each of a plurality of the second detection means.

<Invention 13>

The defect analysis device described in any one of inventions 10 to 12, wherein when the signal processing means detect the formation of defect in the pipe, the vibration means start to apply the vibration and the first detection means detect the vibration applied by the vibration means.

<Invention 14>

A defect analysis method of which a computer executes:

a vibration step of applying vibration with a plurality of frequency components to at least one of fluid flowing in a pipe and the pipe, a first detection step of detecting the vibration applied in the vibration step, and a signal processing step of extracting a feature amount from a vibration waveform acquired in the first detection step and estimating a degree of defect formed in the pipe by using the extracted feature amount.

<Invention 14-2>

The defect analysis method described in invention 14, wherein in the signal processing step, at least one of a peak frequency and a sharpness of a peak is extracted as the feature amount.

<Invention 14-3>

The defect analysis method described in invention 14 or invention 14-2, wherein in the signal processing step, at least one of a size of a hole formed in the pipe and an amount of fluid which leaks to the outside of the pipe through the hole formed in the pipe is estimated as the degree of the defect formed in the pipe.

<Invention 14-4>

The defect analysis method described in any one of inventions 14 to 14-3, wherein the computer stores reference data in which the feature amount is associated with information indicating the degree of defect formed in the pipe and retrieves the reference data by using the feature amount as a key and estimates the degree of defect formed in the pipe in the signal processing step.

<Invention 14-5>

The defect analysis method described in invention 14-4, wherein the computer further executes a pipe information acquisition step of acquiring information about the pipe in which the defect exists, stores the reference data for each of the information about the pipe, and specifies the reference data to be retrieved by using the information about the pipe acquired in the pipe information acquisition step and retrieves the specified reference data by using the feature amount as the key in the signal processing step.

<Invention 14-6>

The defect analysis method described in any one of inventions 14 to 14-5, wherein in the vibration step, the vibration is applied to at least one of the fluid flowing in the pipe in which the defect is detected and the pipe and in the first detection step, the vibration radiated to the outside of the pipe through the defect is detected.

<Invention 14-7>

The defect analysis method described in any one of inventions 14 to 14-6, wherein a vibration unit which applies the vibration in the vibration step is installed on the outer surface of the pipe or the outer surface of a branch pipe connected to the pipe.

<Invention 14-8>

The defect analysis method described in any one of inventions 14 to 14-7, wherein the pipe is installed under the ground and a first detection unit which detects the vibration in the first detection step is installed on the surface of the ground and detects the vibration that is radiated to the outside of the pipe and reaches the surface of the ground.

<Invention 14-9>

The defect analysis method described in invention 14-8, wherein in the first detection step, the first detection unit can be moved to a plurality of different locations on the surface of the ground and detect the vibration at each of a plurality of the installation locations and in the signal processing step, the location of the defect formed in the pipe is specified by using a plurality of vibration waveforms acquired at each of a plurality of the installation locations by the first detection unit.

<Invention 14-10>

The defect analysis method described in any one of inventions 14 to 14-9, wherein the computer further executes a second detection step of detecting at least one of the vibration propagating through the pipe and the vibration propagating through the fluid flowing in the pipe and detects the formation of defect in the pipe by using the vibration detected in the second detection step in the signal processing step.

<Invention 14-11>

The defect analysis method described in invention 14-10, wherein a second detection unit which detects the vibration in the second detection step is installed on the outer surface of the pipe or the outer surface of the branch pipe connected to the pipe.

<Invention 14-12>

The defect analysis method described in invention 14-11, wherein a plurality of the second detection units are used and installed at a predetermined interval and in the signal processing step, a coarse indication of the location of the defect formed in the pipe is specified by using the vibration detected by each of a plurality of the second detection units.

<Invention 14-13>

The defect analysis method described in any one of inventions 14-10 to 14-12, wherein when the formation of defect in the pipe is detected in the signal processing step, application of vibration is started in the vibration step and the vibration is detected in the first detection step.

<Invention 15>

A program which causes a computer to function as:

vibration means for applying vibration with a plurality of frequency components to at least one of fluid flowing in a pipe and the pipe, first detection means for detecting the vibration applied by the vibration means, and signal processing means for extracting a feature amount from a vibration waveform acquired by the first detection means and estimate a degree of defect formed in the pipe by using the extracted feature amount.

<Invention 15-2>

The program described in invention 15, which causes the signal processing means to extract at least one of a peak frequency and a sharpness of a peak as the feature amount.

<Invention 15-3>

The program described in invention 15 or invention 15-2, which causes the signal processing means to estimate at least one of a size of a hole formed in the pipe and an amount of fluid which leaks to the outside of the pipe through the hole formed in the pipe as a degree of defect formed in the pipe.

<Invention 15-4>

The program described in any one of inventions 15 to 15-3, which causes the computer to further function as reference data storage means for storing reference data in which the feature amount is associated with information indicating the degree of defect formed in the pipe and make the signal processing means retrieve the reference data by using the feature amount as a key and estimate the degree of defect formed in the pipe.

<Invention 15-5>

The program described in invention 15-4, which causes the computer to further function as pipe information acquisition means for acquiring information about the pipe in which defect exists, make the reference data storage means store the reference data for each of the information about the pipe, and make the signal processing means specify the reference data to be retrieved by using the information about the pipe acquired by the pipe information acquisition means and retrieve the specified reference data by using the feature amount as the key.

<Invention 15-6>

The program described in any one of inventions 15 to 15-5, which causes the vibration means to apply the vibration to at least one of the fluid flowing in the pipe in which the defect is detected and the pipe and the first detection means to detect the vibration radiated to the outside of the pipe through the defect.

<Invention 15-7>

The program described in any one of inventions 15 to 15-6, which causes the vibration means to make a vibration unit installed on the outer surface of the pipe or the outer surface of the branch pipe connected to the pipe apply the vibration.

<Invention 15-8>

The program described in any one of inventions 15 to 15-7, wherein the pipe is installed under the ground and the program is a program which causes the first detection means to detect the vibration that is radiated to the outside of the pipe and reaches the surface of the ground.

<Invention 15-9>

The program described in invention 15-8, which causes the first detection means to detect the vibration at each of a plurality of installation locations when the first detection means are moved to a plurality of different locations on the surface of the ground and the signal processing means to specify the location of defect formed in the pipe by using a plurality of vibration waveforms acquired at each of a plurality of the installation locations by the first detection means.

<Invention 15-10>

The program described in any one of inventions 15 to 15-9, which causes the computer to further function as second detection means for detecting at least one of the vibration propagating through the pipe and the vibration propagating through the fluid flowing in the pipe and make the signal processing means detect the formation of defect in the pipe by using the vibration detected by the second detection means.

<Invention 15-11>

The program described in invention 15-10, which causes the second detection means to make a sensor installed on the outer surface of the pipe or the outer surface of the branch pipe connected to the pipe detect the vibration.

<Invention 15-12>

The program described in invention 15-11, wherein a plurality of the sensors are used when the second detection means detect the vibration and a plurality of the sensors are installed at a predetermined interval and the program is a program which causes the signal processing means to specify a coarse indication of the location of the defect formed in the pipe by using the vibration detected by each of a plurality of the sensors.

<Invention 15-13>

The program described in any one of inventions 15-10 to 15-12, which causes the vibration means to start to apply the vibration and the first detection means to detect the vibration applied by the vibration means after the signal processing means detect the formation of defect in the pipe.

This application is based upon and claims the benefit of priority from Japanese patent application No. 2012-216890, filed on Sep. 28, 2012, the disclosure of which is incorporated herein in its entirety by reference.

The invention claimed is:

1. A defect analysis device including:
   vibration means for applying vibration with a plurality of frequency components to at least one of fluid flowing in a pipe and the pipe,
   first detection means for detecting the vibration applied by the vibration means, and
   signal processing means for extracting a feature amount from a vibration waveform acquired by the first detection means and for estimating a degree of defect formed in the pipe by using the extracted feature amount.

2. The defect analysis device according to claim 1, wherein
   the signal processing means extracts at least one of a peak frequency and a sharpness of a peak as the feature amount.

3. The defect analysis device according to claim 1, wherein
   the signal processing means estimates at least one of a size of a hole formed in the pipe and an amount of fluid which leaks to the outside of the pipe through the hole formed in the pipe as a degree of defect formed in the pipe.

4. The defect analysis device according to claim 1, wherein
   the defect analysis device further includes reference data storage means for storing reference data in which the feature amount is associated with information indicating the degree of defect formed in the pipe, and
   the signal processing means retrieves the reference data by using the feature amount as a key and estimates the degree of defect formed in the pipe.

5. The defect analysis device according to claim 4, wherein
   the defect analysis device further includes pipe information acquisition means for acquiring information about the pipe in which defect exists,
   the reference data storage means stores the reference data for each of the information about the pipe, and
   the signal processing means specifies the reference data to be retrieved by using the information about the pipe acquired by the pipe information acquisition means and retrieves the specified reference data by using the feature amount as the key.

6. The defect analysis device according to claim 1, wherein
   the vibration means applies the vibration to at least one of the fluid flowing in the pipe in which defect is detected and the pipe, and
   the first detection means detects the vibration radiated to the outside of the pipe through the defect.

7. The defect analysis device according to claim 1, wherein
   the vibration means is installed on the outer surface of the pipe or the outer surface of a branch pipe connected to the pipe.

8. The defect analysis device according to claim 1, wherein
   the pipe is installed under the ground, and
   the first detection means is installed on the surface of the ground and detects the vibration that is radiated to the outside of the pipe and reaches the surface of the ground.

9. The defect analysis device according to claim 8, wherein
   the first detection means is configured to be moved to a plurality of different locations on the surface of the ground and to detect the vibration at each of a plurality of the installation locations, and
   the signal processing means uses a plurality of vibration waveforms acquired at each of a plurality of the installation locations by the first detection means and specifies the location of the defect formed in the pipe.

10. The defect analysis device according to claim 1, wherein
    the defect analysis device further includes second detection means for detecting at least one of the vibration propagating through the pipe and the vibration propagating through the fluid flowing in the pipe, and
    the signal processing means detects the formation of defect in the pipe by using the vibration detected by the second detection means.

11. The defect analysis device according to claim 10, wherein
    the second detection means is installed on the outer surface of the pipe or the outer surface of the branch pipe connected to the pipe.

12. The defect analysis device according to claim 10, wherein
    the defect analysis device includes a plurality of the second detection means and the plurality of the second detection means are installed at a predetermined interval, and
    the signal processing means specifies a coarse indication of the location of the defect formed in the pipe by using the vibration detected by the plurality of the second detection means.

13. The defect analysis device according to claim 10, wherein
    when the signal processing means detects the formation of defect in the pipe, the vibration means applies the vibration and the first detection means detects the vibration applied by the vibration means.

14. A defect analysis method in which a computer processor executes the steps of:
    applying vibration with a plurality of frequency components to at least one of fluid flowing in a pipe and the pipe,
    detecting the applied vibration with the plurality of frequency components,
    extracting a feature amount from a vibration waveform acquired in detecting the applied vibration, and
    estimating a degree of defect formed in the pipe by using the extracted feature amount.

15. The defect analysis method according to claim 14, wherein
    in extracting the feature amount, at least one of a peak frequency and a sharpness of a peak is extracted as the feature amount.

16. The defect analysis method according to claim 14, wherein the computer processor further executes the steps of:
    detecting at least one of the vibration propagating through the pipe and the vibration propagating through the fluid flowing in the pipe, and
    detecting the formation of defect in the pipe by using the detected vibration.

17. The defect analysis method according to claim 16, wherein
    when the formation of defect in the pipe is detected, application of vibration is started and the applied vibration is detected.

18. A non-transitory computer-readable medium, storing a program which when executed by a computer causes the computer to perform a method comprising:
   applying vibration with a plurality of frequency components to at least one of fluid flowing in a pipe and the pipe,
   detecting the vibration applied by the vibration means,
   extracting a feature amount from a vibration waveform acquired by the computer, and
   estimating a degree of defect formed in the pipe by using the extracted feature amount.

19. The non-transitory computer-readable storage medium, storing the program according to claim 18, which when executed by the computer, further causes the computer to perform the steps of:
   detecting at least one of the vibration propagating through the pipe and the vibration propagating through the fluid flowing in the pipe, and
   detecting the formation of defect in the pipe by using the detected vibration.

20. The non-transitory computer-readable medium, storing the program according to claim 19, which when executed by the computer, further causes the computer to perform the steps of:
   applying the vibration, and
   detecting the applied vibration after detecting the formation of the defect in the pipe.

* * * * *